United States Patent [19]

Tan

[11] Patent Number: 5,160,044
[45] Date of Patent: Nov. 3, 1992

[54] PROCESS FOR SEPARATING ETHANOL FROM AQUEOUS SOLUTION

[75] Inventor: Chung-Sung Tan, Taipei, Taiwan

[73] Assignee: National Tsing Hua University, Hsingchu, Taiwan

[21] Appl. No.: 839,206

[22] Filed: Feb. 20, 1992

[51] Int. Cl.$^5$ .................. B01D 11/00; B01D 61/00
[52] U.S. Cl. .................. 210/634; 210/651; 210/652; 426/14
[58] Field of Search .......... 210/652, 640, 649, 634, 210/651, 639, 636; 55/158, 16; 426/592, 14

[56] References Cited

U.S. PATENT DOCUMENTS

| | | | |
|---|---|---|---|
| 4,612,196 | 9/1986 | Golstein et al. | 426/592 |
| 4,663,050 | 5/1987 | Li et al. | 210/649 |
| 4,717,482 | 1/1988 | Light | 210/651 |
| 4,770,780 | 9/1988 | Moses | 210/634 |
| 4,792,402 | 12/1988 | Fricker | 210/652 |
| 4,806,366 | 2/1989 | Dick et al. | 210/651 |
| 4,824,570 | 4/1989 | Bethuel et al. | 210/634 |
| 4,888,189 | 12/1989 | Gnekow | 210/652 |
| 4,983,303 | 1/1991 | Ugami | 210/640 |
| 4,990,350 | 2/1991 | Rohmann | 210/652 |
| 4,999,209 | 3/1991 | Gnekow | 426/592 |
| 5,032,279 | 7/1991 | Lee | 210/500.28 |
| 5,093,141 | 3/1992 | Nemeth et al. | 426/14 |

Primary Examiner—Robert A. Dawson
Assistant Examiner—Ana M. Fortuna
Attorney, Agent, or Firm—Fish & Richardson

[57] ABSTRACT

The present invention provides a process for separating ethanol from an aqueous solution by supercritical or near supercritical extraction in combination with reverse osmosis, which includes contacting an ethanol containing aqueous solution with one side of a reverse osmosis membrane in the presence of a supercritical or near supercritical $CO_2$ having a pressure of 72.8–88.4 atm and a temperature of 26.5°–34° C., wherein the volumetric ratio of the supercritical or near supercritical $CO_2$ to the ethanol containing aqueous solution is higher than 1.8, and recovering a permeate solution having a lower ethanol concentration from the opposite side of the membrane.

7 Claims, 12 Drawing Sheets

PROCESS FOR SEPARATING ETHANOL FROM AQUEOUS SOLUTION

FIELD OF THE INVENTION

The present invention relates to separation of ethanol from an aqueous solution containing ethanol, especially to the separating of ethathol from the aqueous solution by a method incorporation supercritical or near supercritical $CO_2$ with reverse osmosis.

BACKGROUND OF THE INVENTION

Recovery or removal of ethanol from aqueous solutions is needed in many industrial processes and in the clean-up of waste streams. Recently increased use of fermentation to produce ethanol also leads to recovery problem of this kind. Because of relatively great affinity between ethanol and water, significant energy is required to achieve separation using the conventional evaporation and distillation techniques. Many attempts therefore have been made to develop less energy-intensive separation alternatives which include adsorption, liquid extraction, reverse osmosis membrane processes, and supercritical fluid extraction.

Because supercritical carbon dioxide possesses several special characteristics and physicochemical properties, such as nonflammable, nontoxic, inexpensive, higher mass transfer rate, and adjustable extraction power for organic compounds varying with the density, it has been recognized to be a good solvent for extraction of organic compounds from aqueous solution. Despite of low distribution ratio for dilute aqueous solutions and phase complexity near the critical point of carbon dioxide, as well as several technical problems remain to be solved such as clean-up and recompression of recycled carbon dioxide, to extract ethanol from aqueous solutions by supercritical carbon dioxide seems to be superior to distillation technique from the energy point of view. McHugh and Krukonis in their book, entitled "Supercritical Fluid Extraction Principles and Practice", Butterworth, Stoneham, MA (1986), have extensively described the supercritical fluid extraction, details thereof are incorporated by reference.

Ethanol separation by reverse osmosis membrane process has been a subject over the past years. The reverse osmosis can be illustrated by its application in sea water purification. Imagine a box divided into two chambers by a rigid, semipermeable membrane that allows water to pass through it but does not allow the passage of solutes contained in sea water. In the left chamber we put pure water, and in the right, we put sea water. Since water activity in the left (pure water chamber) higher than that in the right (sea water chamber), water will flow through the membrane from left to right and dilute the sea water. This phenomenon is called osmosis. If the pressure of sea water chamber is increased gradually, the osmosis phenomenon will become insignificant. When the increase of pressure stops water flowing through the membrane from left to right, the extra pressure applied is called osmotic pressure. If the pressure applied in the right chamber (sea water) is higher than the osmotic pressure, water in the right (sea water) chamber will flow through the membrane to the left (pure water) chamber. As a result, water is recovered from the sea water chamber. This phenomenon is called reverse osmosis. In separating a solution by reverse osmosis, the solution to be separated flows on one side of a membrane, the solution collected on the other side is called permeate and the solution remained on the same side is called retentate. The separation effectiveness is generally determined by the rejection rate, R, of a subject solute, which is defined as follows, and the permeation rate of the solution $$R = (C_{in} - C_{perm})/C_{in} \times 100\% \qquad (I)$$

wherein
$C_{in}$ is the concentration of a subject solute in the feed solution;
$C_{perm}$ is the concentration of the subject solute in the permeate.

According to the definition, a higher rejection rate represents a better separation effectiveness.

In most of the membrane separation process a plurality of membranes are used as a module. Typical modules including spiral type, tubular type, hollow fiber and frame/plate type. The reverse osmosis systems in general use the spiral type module. The membrane can be classified by its synthesizing method, for example a dense film, an asymmetric film, or a composite film. A dense film is suitable for using in a high pressure separating operation, which is homogeneous and is synthesized uniformly. An asymmetric film is synthesized under nonhomogenous conditions, each surface of which has a different density. The asymmetric film is used in a relatively low pressure reverse osmosis separation. A composite film is prepared by modifying a dense film or an asymmetric film or by blending several different polymeric films. A recently developed composite film is directly synthesized. The composite films in the prior art mostly are specially designed for separating certain particular solutions.

In the prior attempts for separating ethanol from an aqueous solution by reverse osmosis, it is found that the separation effectiveness is not satisfactory because water molecules in the membrane matrix tend to form dimers which have a molecular weight very close to that of ethanol.

To enhance separation effectiveness, one of the approaches is to synthesize new membranes or to modifty the existing membranes, and the other approach is to develop new separation processes. Pervaporation and perstraction are two examples for the latter one in which a low-pressure vapor or a purge organic liquid is allowed to flow along one face of a membrane, while the feed flows along the opposite face. A better separation provided by these processes over the use of membrane alone may be due to the addition of a driving force for mass transfer. Particular references are as follows:

1) "Observations on the Performances of Pervaporation under Varied Conditions. In Membranes and Membrane Process" by Rautenbach and Albercht; Drioli, E., Nakagaki, M. Eds.; Plenum Co.: New York, 1986, p 595–607.

2) "Separation of Liquid Benzene/Cyclohexane Mixtures by Perstraction and Pervaporation" *J. Membrane Sci.* 1988, 77, 205–232, by Acharya et al.

3) "Sorption, Diffusion, and Pervaporation of Organics in Polymer Membranes" *J. Membrane Sci.* 1989, 44, 161–181, by Lee et al.

4) "On the Prediction of Separation Factor and Permeability in the Separation of Binary Mixtures by Pervaporation" *J. Membrane Sci.* 1989, 46, 335–348, by Rhim and Hwang.

5) "A Study on Characteristics and Enhancement of Pervaporation-Membrane Separation Process" *Desalination* 1989, 71, 1–18, by Zhu et al.

The object of present invention is to provide an improved process for ethanol separation from an aqueous solution by incorporating supercritical carbon monoxide with reverse osmosis.

SUMMARY OF THE INVENTION

The present invention provides a process for separating ethanol from an aqueous solution by supercritical or near supercritical extraction in combination with reverse osmosis comprising contacting an ethanol containing aqueous solution with one side of a reverse osmosis membrane in the presence of a supercritical or near supercritical $CO_2$ having a pressure of 72.8–88.4 atm and a temperature of 26.5°–34° C., wherein the volumetric ratio of $CO_2$ to said ethanol containing aqueous solution at said pressure and temperature is higher than 1.8, and recovering a permeate solution having an ethanol concentration lower than that of said ethanol containing aqueous solution from the opposite side of said membrane.

Preferably, the pressure and temperature of said supercritical or near supercritical $CO_2$ are 74.8–81.6 atm and 31.1°–32.5° C., respectively, and the pressure on the opposite side of the membrane is atmospheric pressure.

Preferably, the volumetric ratio of $CO_2$ to said ethanol containing aqueous solution is higher than 4, and the higher the ratio, the better the separation.

The ethanol containing aqueous solution may also contain a solute other than ethanol, and the ethanol concentration thereof is less than 10 wt %. Moreover, a better separation effectiveness is observed in the present process as the ethanol concentration decreases.

In practise, an ethanol containing aqueous solution can be sequentially subjected to a series of present separation treatments.

DETAILED DESCRIPTION OF THE INVENTION

Figure 1:
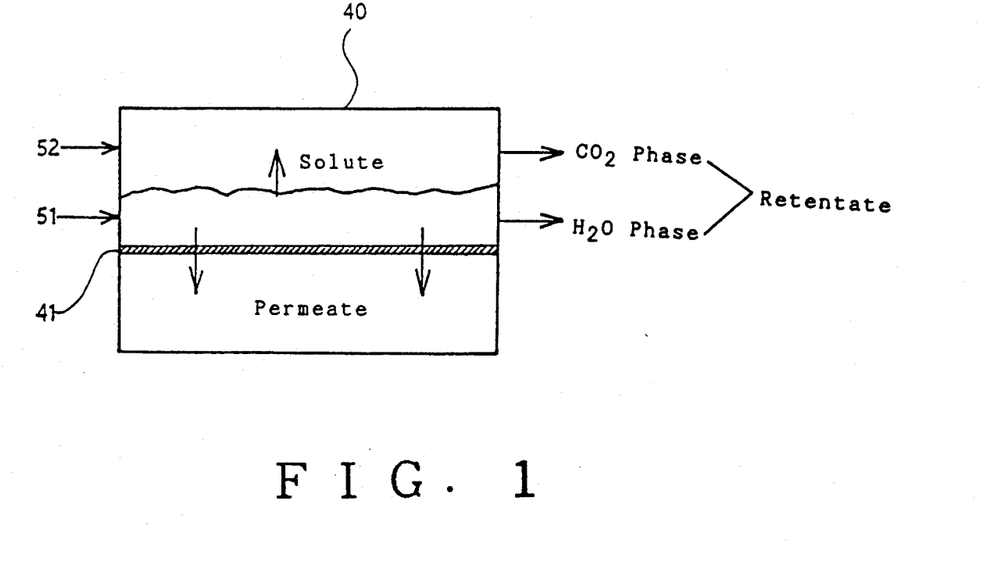
FIG. 1 is a schematic diagram which shows the separation process of present invention.

Referring to FIG. 1, a process according to present invention is illustrated, in which an ethanol containing aqueous solution feed stream 51 and a supercritical or near supercritical $CO_2$ stream 52 are introduced into an upper chamber of a membrane holder 40 having a reverse osmosis membrane 41. The membrane holder 40 is divided into two chambers by the membrane 41. Because the supercritical or near supercritical $CO_2$ has a lower density than that of the aqueous solution and a higher ethanol solubility than that of water, the $CO_2$ stream 52 will flow on the top of the aqueous solution stream 51 and will extract ethanol solute from the aqueous solution stream 51. As a result, the ethanol concentration of aqueous solution stream 51 will be reduced due to this extraction. Consequently, the ethanol concentration of the permeate will decrease and the ethanol rejection rate will increase. In the present process, the extraction of ethanol from the aqueous solution to the supercritical or near supercritical $CO_2$ provides a force for driving ethanol away from the membrane.

Details of the present invention can be further understood by the following examples, which are meant to illustrate the present invention and are not meant to be limiting.

EXAMPLE

Figure 2:
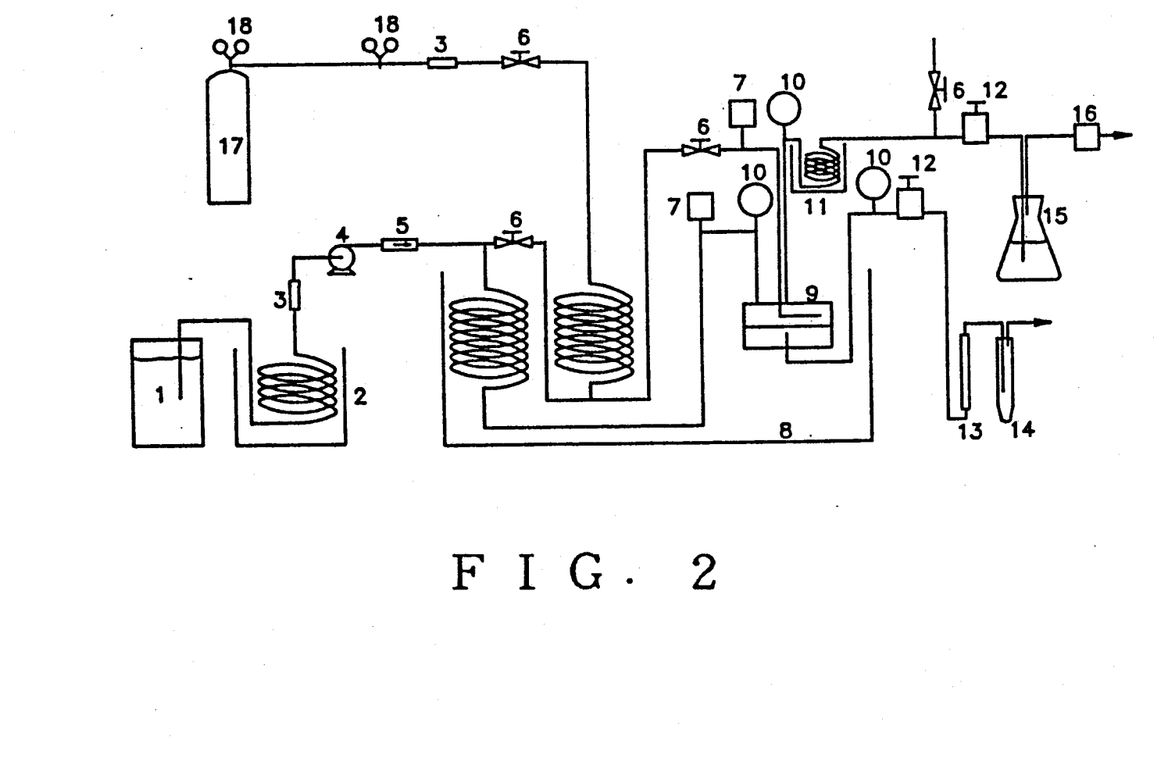
FIG. 2 is a schematic diagram which shows the experimental apparatus suitable for using in the present process, wherein 1 represents an ethanol solution tank; 2 represents an ice bath; 3 represents a filter; 4 represents a minipump; 5 represents a check valve; 6 represents a metering valve; 7 represents a temperature indicator; 8 represents a constant temperature bath; 9 represents a membrane holder; 10 represents a pressure gauge; 11 represents an oil bath; 12 represents a back pressure regulator; 13 represents a pipette; 14 represents a burette; 15 represents a separator; 16 represents a wet gas meter; 17 represents a $CO_2$ cylinder, and 18 represents a regulator.

FIG. 2 shows an experimental apparatus suitable for carrying out the present process, which includes collecting and measuring devices for the retentate and permeate.

The membrane used in this work was an aromatic polyamine thin-film composite membrane which was purchased from FilmTec Corp. with a mark name FT-30. The reasons for using this membrane are that it is commercially available and it shows its superiority to deal with ethanol-water separation over other reverse osmosis membranes ("Comparison of Membrane Processes with Distillation Alcohol/Water Separation" *J. Membrane Sci.* 1982, 12, 1–26, by Mehta). The FT-30 membrane was stored under conditions specified by the manufacturer and was used without further treatment. A flat sheet membrane was placed in a membrane holder (Milipore Co., 93700) and was supported by a porous sintered stainless steel powder block. The volumes of the upper and lower chambers were about 2 ml in each. The effective area of the membrane was about 9.5 cm$^2$.

All of the tubing, valves and gauges used in the apparatus of FIG. 2 were entirely composed of 316 stainless steel. The aqueous solutions were prepared by adding a known amount of ethanol of a purity 99.8% into deionized water and mixing them thoroughly. The prepared aqueous solution was compressed by a minipump 4 (Milton Roy, 396-89) and was heated by a preheating coil immersed in a constant temperature bath 8 to the desired pressure and temperature, respectively. The accuracy of the constant temperature bath 8 was within 0.3° K. High pressure carbon dioxide of a purity 99.8% was stored in a high pressure tank 17. The pressure of the $CO_2$ stream was adjusted by regulators 18 and metering valves 6 and the temperature of $CO_2$ was controlled in a constant temperature bath 8 through a preheating coil. The pressures and temperatures varied from 65.3 to 88.4 atm and 299° to 310° K., respectively. Two types of operation were performed to observe the effect of contact time between $CO_2$ and aqueous solution on separation effectiveness: 1) the $CO_2$ stream and the aqueous solution premixed first before they entered the upper chamber of the membrane holder 9, and 2) these two streams flowed into the upper chamber separately. For the latter operation, the aqueous solution was fed to the upper chamber through a $\frac{1}{8}''$ tube and the $CO_2$ was fed to the upper chamber through a 1/16" tube which was inserted into the above $\frac{1}{8}''$ tube and flowed tangentially in the chamber. However, the experimental results showed that these two types of operation provided almost the same ethanol rejection.

The effluent stream of the upper chamber (retentate) was depressurized through a back pressure regulator 12 (Tescom, TC-06) and passed through a separator 15 where the condensed liquid was collected. 1.0 µl of the condensed solution was analyzed frequently by a gas chromatography (Varian, 3700) to determine the concentration of ethanol. The composition of the gas phase leaving from the separator 15 was also analyzed by GC, however, no ethanol was detected. The amount of $CO_2$ in the retentate stream was measured by a wet test meter 16 (Yokogawa, W-NK-1B) which located at the downstream of the separator 15.

The pressure of the lower chamber was maintained at 1 atm. Because the amount of $CO_2$ in the effluent stream of the lower chamber (permeate) was not large enough (about 200 to 400 ml/hr at ambient condition) to be measured accurately by the wet test meter, it was determined by the device of a 1.0 ml pipette 13 whose diameter of 0.2 cm and length of 30 cm followed by a 50 ml burette 14 whose diameter of 1 cm. A gas-liquid separation will take place as the effluent stream enters the burette 14 due to a sudden increase of cross section area by 25 times. The vaporized gas leaves the burette 14 from an upper exit where a demister composed of several layers of 5µ steel net is provided to avoid liquid being entrained by the exit gas. The flow rate of the permeate stream could be read by the rising rate of the bubbles in the pipette 13 and the amount of aqueous solution could be determined from the accumulated liquid level in the burette 14. From these two measured rates, the amount of $CO_2$ could then be determined. The concentration of ethanol in the collected liquid phase was detected frequently by GC.

The reproducibility tests were carried out at several operating conditions. It was observed that the data could be reproduced within 6.0%. The overall mass balance on ethanol was also checked. The sum of the mass of ethanol in the retentate and permeate streams was found to agree well with that in the feed. The deviation was generally less than 2.0%.

In order to provide the basis for comparison, the experiments for reverse osmosis separation of ethanol from ethanol-water solution by FT-30 membrane at various operating temperatures and pressures were also carried out. The separation effectiveness was determined by the ethanol rejection as defined by equation I and the permeation rate. According to the definition, a higher ethanol rejection respresents a better separation effectiveness.

Separation Steps

1) Washing the tubing connected to the upper chamber of the membrane holder 9 with an ethanol solution to be separated by opening all the metering valves except the one connected to the $CO_2$ cylinder 17, whereby the solution contained in said tubing had an identical initial concentration;

2) Closing the valves controlling the gas exits of the tubing connected to the upper chamber of the membrane holder 9, and then adjusting the back pressure regulator 12 and the constant temperature bath 8 at the desired operational pressure and temperature respectively; opening the valves controlling the gas exists of the tubing connected to the lower chamber of the membrane holder 9, i.e. the pressure of lower chamber is atmospheric pressure;

3) Introducing the ethanol solution in tank 1 into the system by a minipump 4 under the operational pressure for a period of 3-4 hours; (This step is called blank run.)

4) After said period starting the introduction of $CO_2$ which is gradually increased from zero to a desired $CO_2$ flow rate in order to prevent the membrane from being damaged by the turbulents caused by a sudden large amount introduction of $CO_2$;

5) Maintaining the flow rates of $CO_2$ and ethanol solution, consistently sampling and analyzing the premeate collected at an interval of 15-30 minutes until the concentrations determined varying within a specified tolerance. (It takes about two hours for the concentrations varying within 1%).

For comparison, the experiments for reverse osmosis separation were also conducted by repeating the above steps except no $CO_2$ being introduced.

Results and Discussion (a) Reverse osmosis separation

Figure 3:
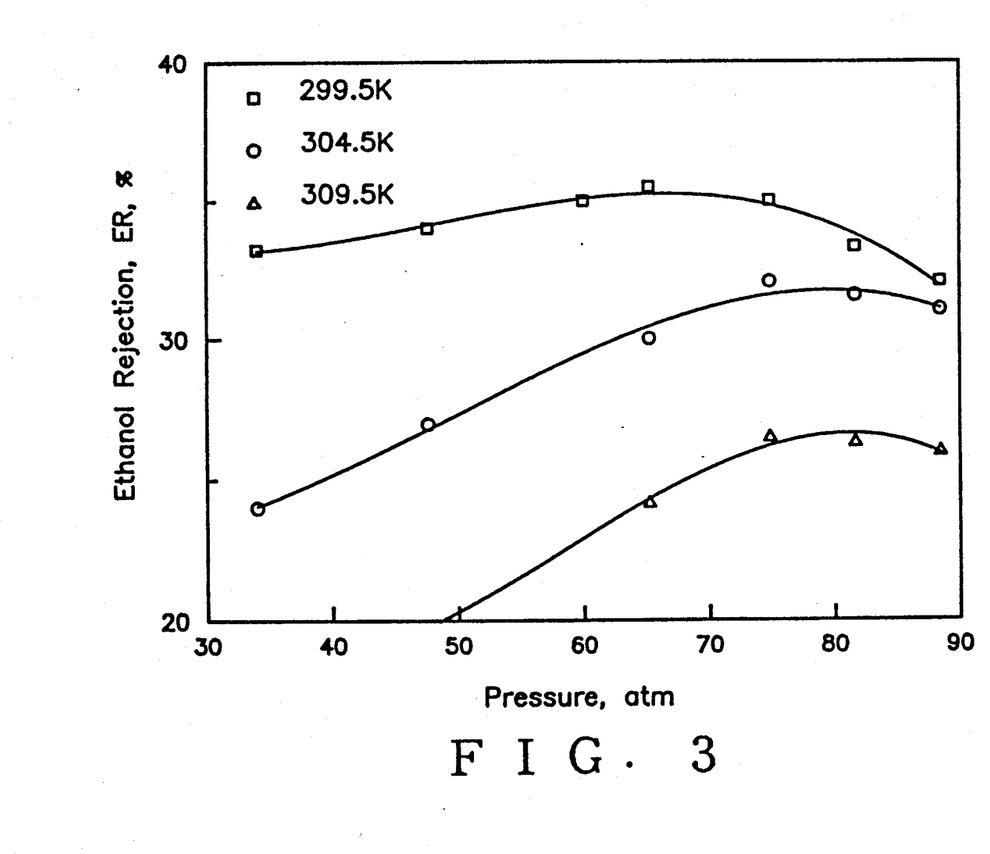
FIG. 3 is a plot which shows ethanol rejection of the reverse osmosis separation.

Table 1 shows the ethanol rejections of the reverse osmosis separation for the aqueous solution containing 6 wt % ethanol. The results of Table 1 are also plotted in FIG. 3.

TABLE 1

| | Ethanol Rejection, %[1] | | | | | |
|---|---|---|---|---|---|---|
| | Pressure, atm | | | | | |
| temp, °K. | 34.0 | 47.6 | 65.3 | 74.8 | 81.6 | 88.4 |
| 299.5 | 33.2 | 34.0 | 35.5 | 35.0 | 33.3 | 32.0 |
| 304.5 | 24.0 | 27.0 | 30.0 | 32.0 | 31.5 | 31.0 |
| 309.5 | — | 19.7 | 24.2 | 26.5 | 26.3 | 26.0 |

[1]Ethanol rejection, R, is defined as above Eq. I.

Figure 4:
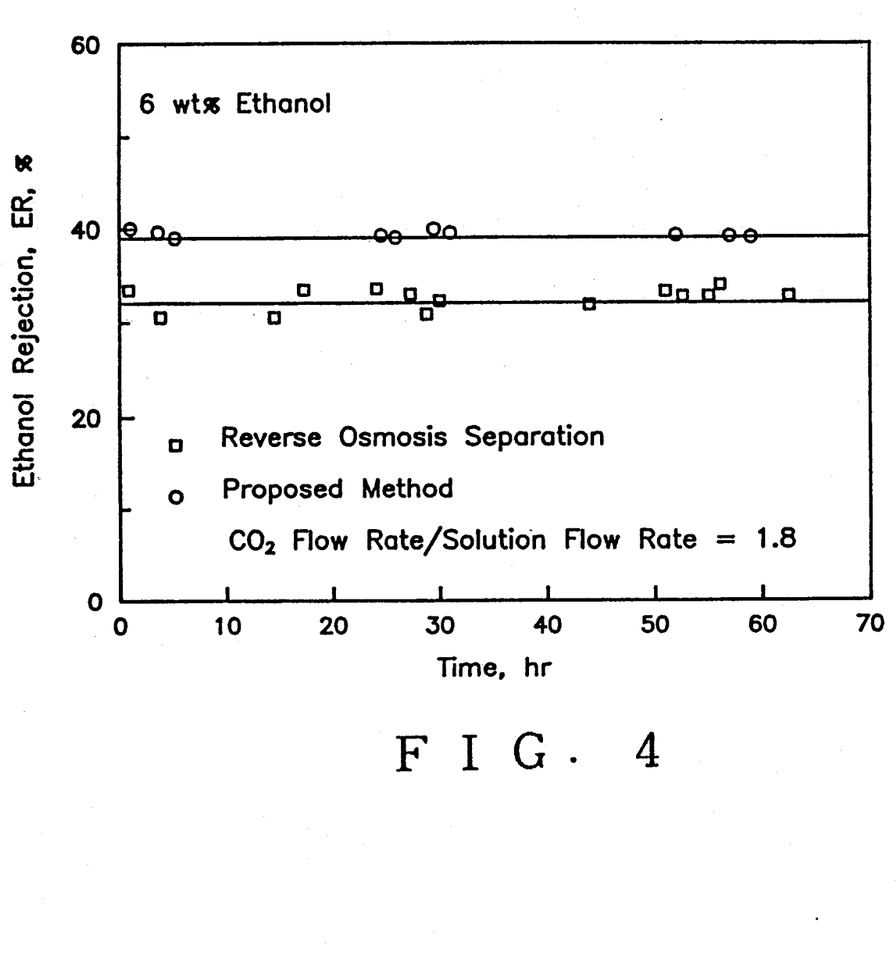
FIG. 4 is a plot which shows the performance of the present process and the reverse osmosis separation within a period of 70 hours.
Figure 5:
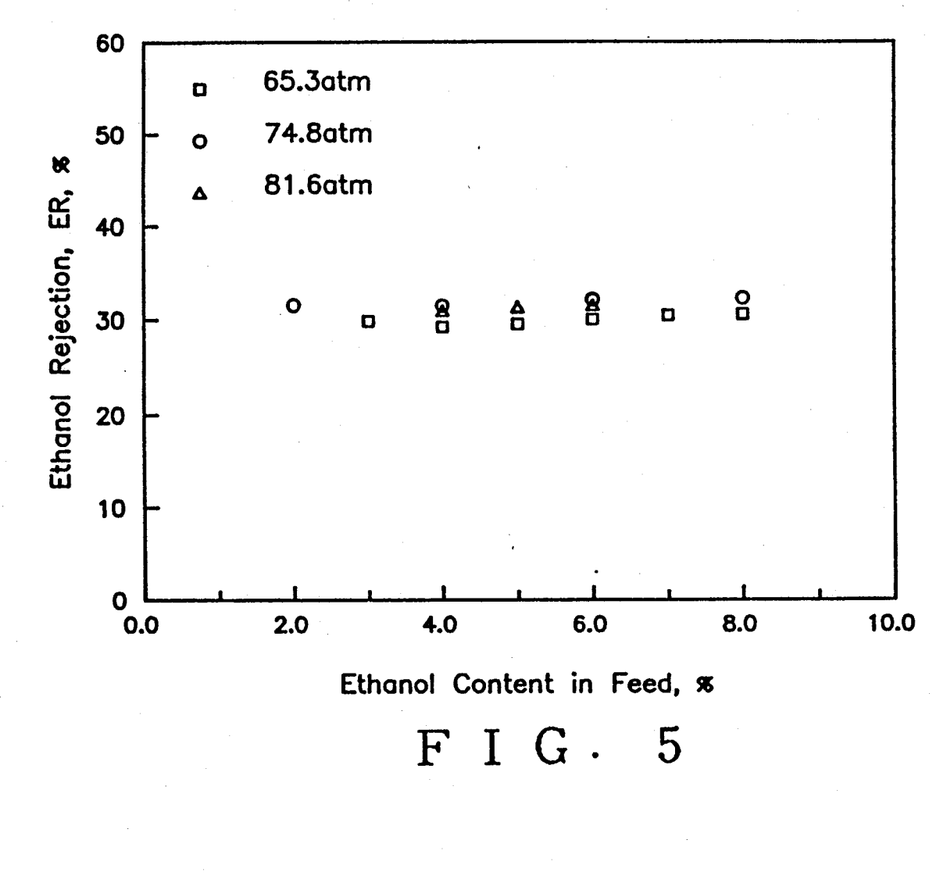
FIG. 5 is a plot which shows ethanol rejection of the reverse osmosis separation at 304.5° K. for various ethanol contents in aqueous solution feed.

The operation was stable within a period of 70 hours, a typical example is shown in FIG. 4. During the measurements, the ethanol rejection was found that not to strongly depend on the ethanol content in the feed solution, this phenomenon is demonstrated in FIG. 5.

As it can be seen from Table 1, the highest ethanol rejection occured at about 299.5° K. and 65.3 atm which resulted in 35.5% ethanol rejection. This was chosen as the basis for comparison, i.e. a relative ethanol rejection, RER, is defined as $$RER = (ER_s - ER_o)/ER_o \quad (II)$$

wherein $ER_s$ is the ethanol rejection for the present process and $ER_o$ is that for the reverse osmosis separation at 299.5° K. and 65.3 atm.

b) Separation by incroporation reverse osmosis with supercritical or near supercritical $CO_2$ The preset separation process carried out by the above-described separation steps 1)–5) was also stable within a period of 70 hours, a typical example is shown in FIG. 4.

Effect of Introduction Time of $CO_2$

At the beginning of this study, supercritical carbon dioxide was introduced immediately with aqueous solution into the membrane holder as soon as its temperature, pressure, and flow rate reached desired values. Under this operation the ethanol rejections were found to be less than those for the reverse osmosis separation at any operating conditions and were hardly to be reproduced, also serious demage on the surface of the membrane was observed. If the introduction time of $CO_2$ was changed to 3–4 hours after the reverse osmosis operation, the above phenomena no longer occurred. This introduction time was found to be slightly dependent on the operating temperature and pressure, however, four hours was observed to be long enough for the presently studied ranges. The possible reason for the need of a delayed introduction time of $CO_2$ is that it takes time to form a gel layer between membrane and ethanol solution which can protect membrane not to be ruined by supercritical $CO_2$.

Effect of Flow Rate of Aqueous Solution

Figure 6:
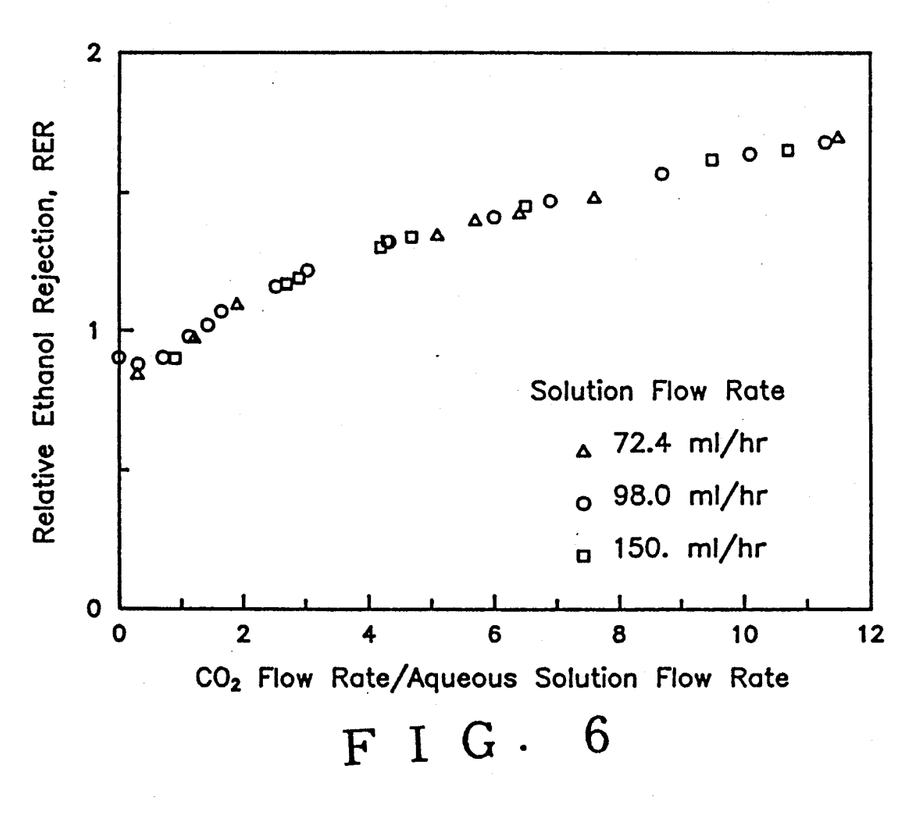
FIG. 6 is a plot which shows relative ethanol rejection at 304.5° K. and 74.8 atm for various aqueous solution flow rates.

FIG. 6 indicates that whenever the ratio of $CO_2$ flow rate to aqueous solution flow rate is fixed, the same ethanol rejection can be obtained for different aqueous solution flow rates.

Effect of Temperature and Pressure

Figure 7:
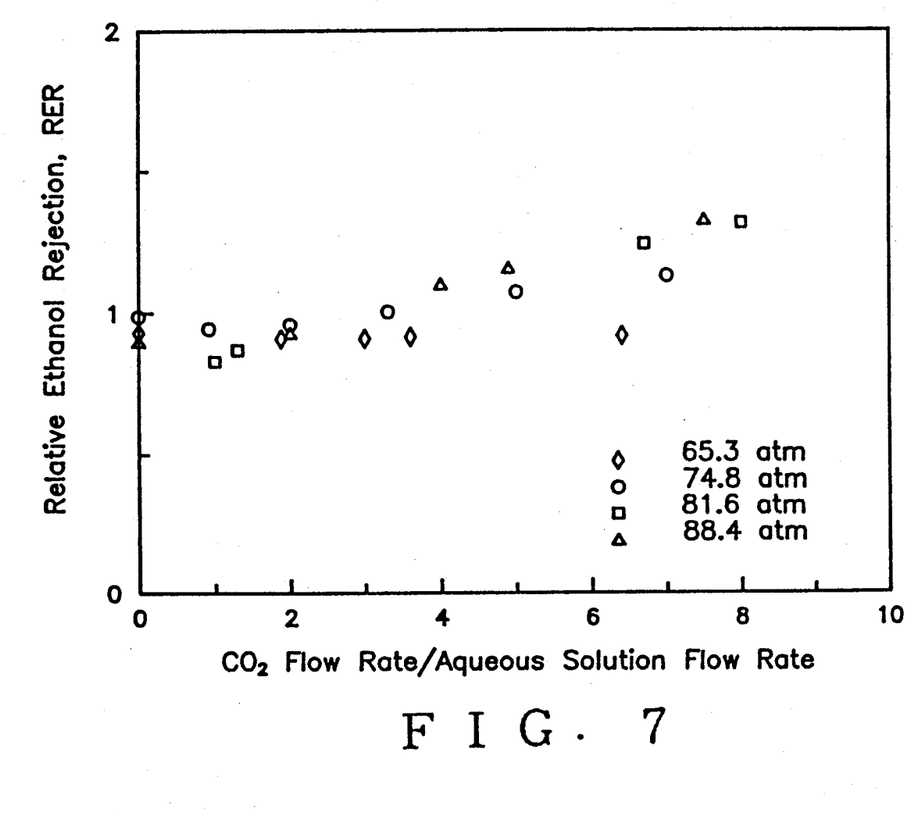
FIG. 7 is a plot which shows relative ethanol rejection of the present process at 299.5° K. for 6 wt % ethanol in the feed.
Figure 8:
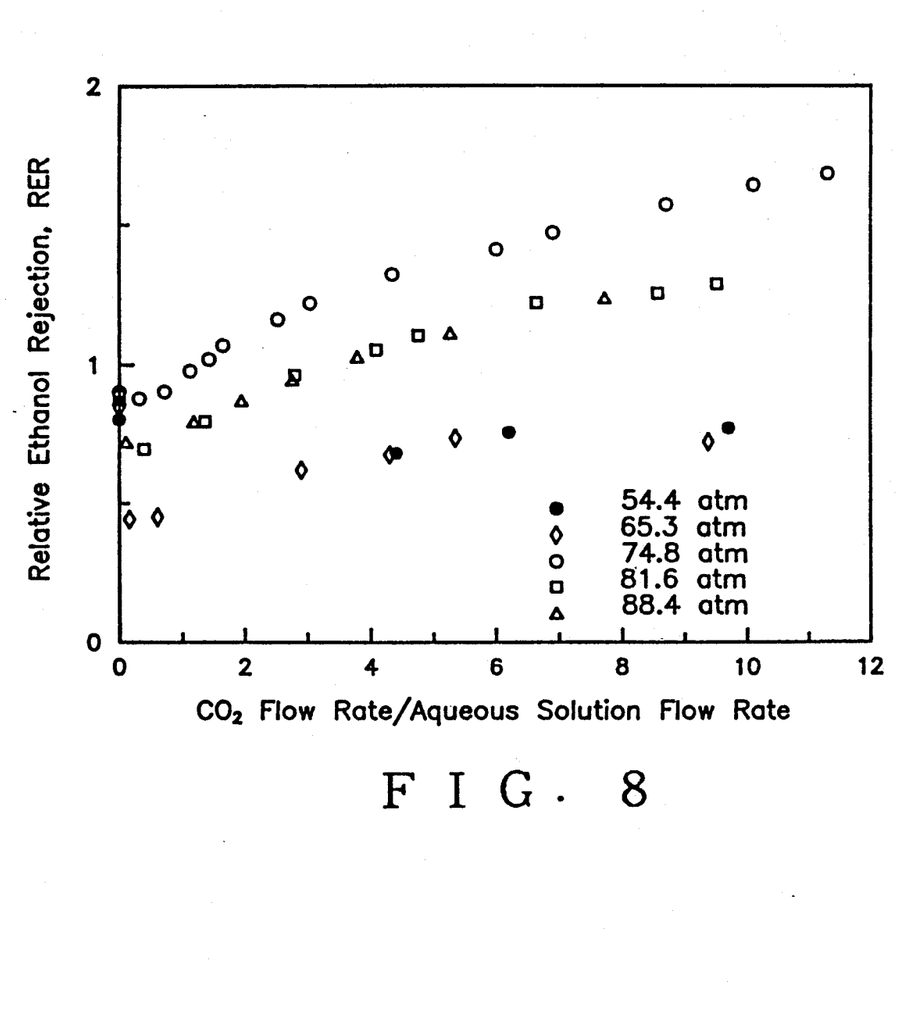
FIG. 8 is a plot which shows relative ethanol rejection of the present process at 304.5° K. for 6 wt % ethanol in the feed.
Figure 9:
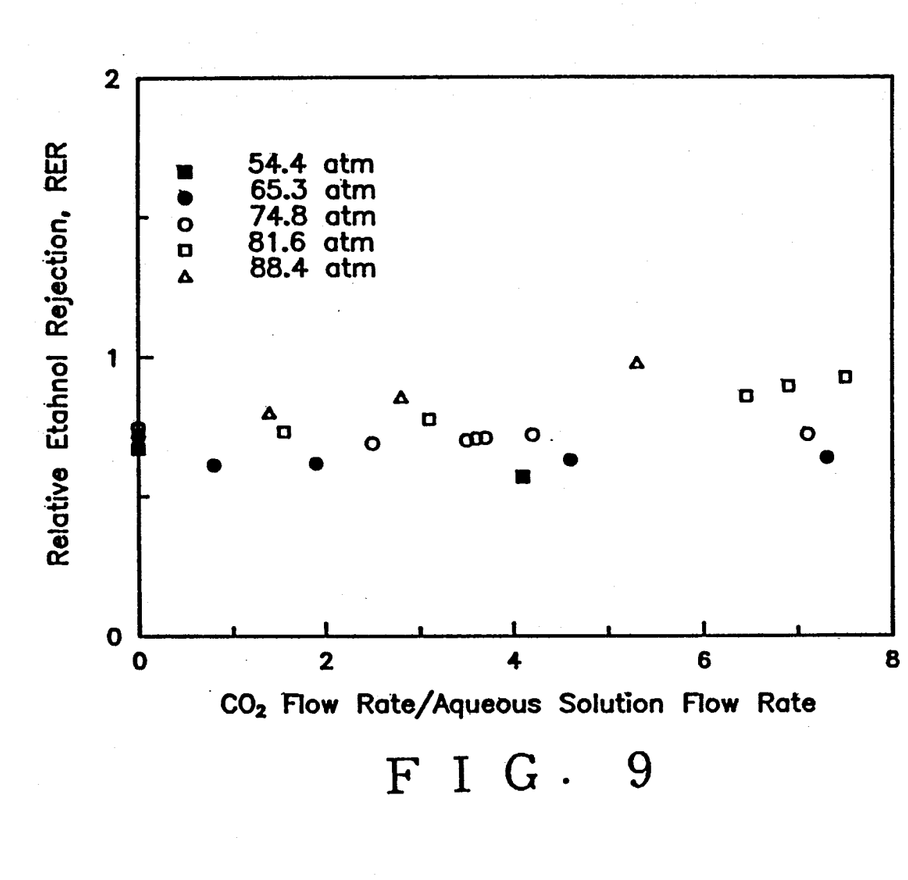
FIG. 9 is a plot which shows relative ethanol rejection of the present process at 309.5° K. for 6 wt % ethanol in the feed.

When the flow rate of the aqueous feed consisting of 6 wt % ethanol was fixed at 98 ml/hr, the relative ethanol rejections at various temperatures and pressures are shown in FIGS. 7 to 9. It can be seen that when the pressure is below the critical pressure of $CO_2$ (72.8 atm), the ethanol rejection using the present process could never exceed that using the reverse osmosis separation (RER<1). The superiority in ethanol rejection of the present process to the reverse osmosis separation generally occurred at relatively higher ratios of $CO_2$ flow rate to aqueous solution flow rate for the pressures larger than the critical pressure of $CO_2$.

From FIGS. 7 to 9 it can also be found that the best ethanol rejection occurred at the operating condition 304.5° K and 74.8 atm which is near the critical point of $CO_2$. At very high ratio of $CO_2$ flow rate to aqueous solution flow rate, the ethanol rejection could be enhanced about 70% as compared with the reverse osmosis separation. However, as shown in FIG. 9 the relative ethanol rejection for T=309.5° K runs are all less than unity.

Figure 10:
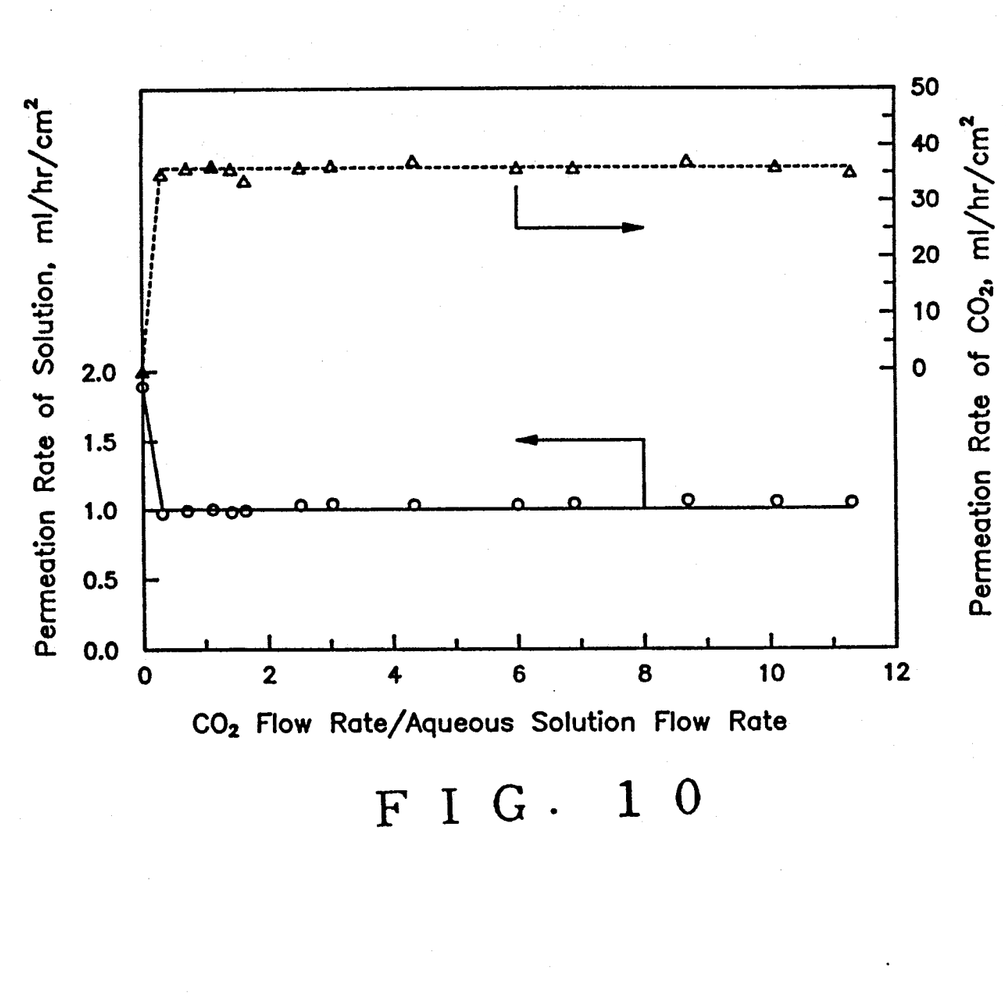
FIG. 10 is a plot which shows permeation rates of aqueous solution and $CO_2$ at 304.5° K. and 74.8 atm.

FIG. 10 illustrates that the permeation rates of aqueous solution and $CO_2$ at 304.5° K. and 74.8 atm kept constant at any ratio of $CO_2$ flow rate to aqueous solution flow rate. The permeation rate of aqueous solution (around 1.05 ml/hr/cm²) is about one-half that for the reverse osmosis separation (about 1.9 ml/hr/cm²). The decrease of permeation rate in the presence of $CO_2$ may be explained as follows. The dissolution of $CO_2$ in aqueous solution results in the change of composition in the liquid phase, consequently the osmotic pressure of water would change significantly, for example, from 27 atm for the reverse osmosis separation (zero $CO_2$ flow rate) to 59 atm at the $CO_2$ flow rate 200 ml/hr. The increase of water osmotic pressure results in the decrease of water permeation. On the other hand, the change of osmotic pressure of ethanol is not significant, for example, from 1179 atm for the reverse osmosis separation to 1185 atm at the $CO_2$ flow rate 200 ml/hr. Since ethanol content in aqueous solution is relatively small, the permeation rate of aqueous solution thus drops compared with that for the reverse osmosis separation. Since the variation of osmotic pressures of water and ethanol is very small at the ratio of $CO_2$ flow rate to aqueous solution flow rate larger than 0.5, the permeation rate is essentially constant.

Effect of Ethanol Content

Figure 11:
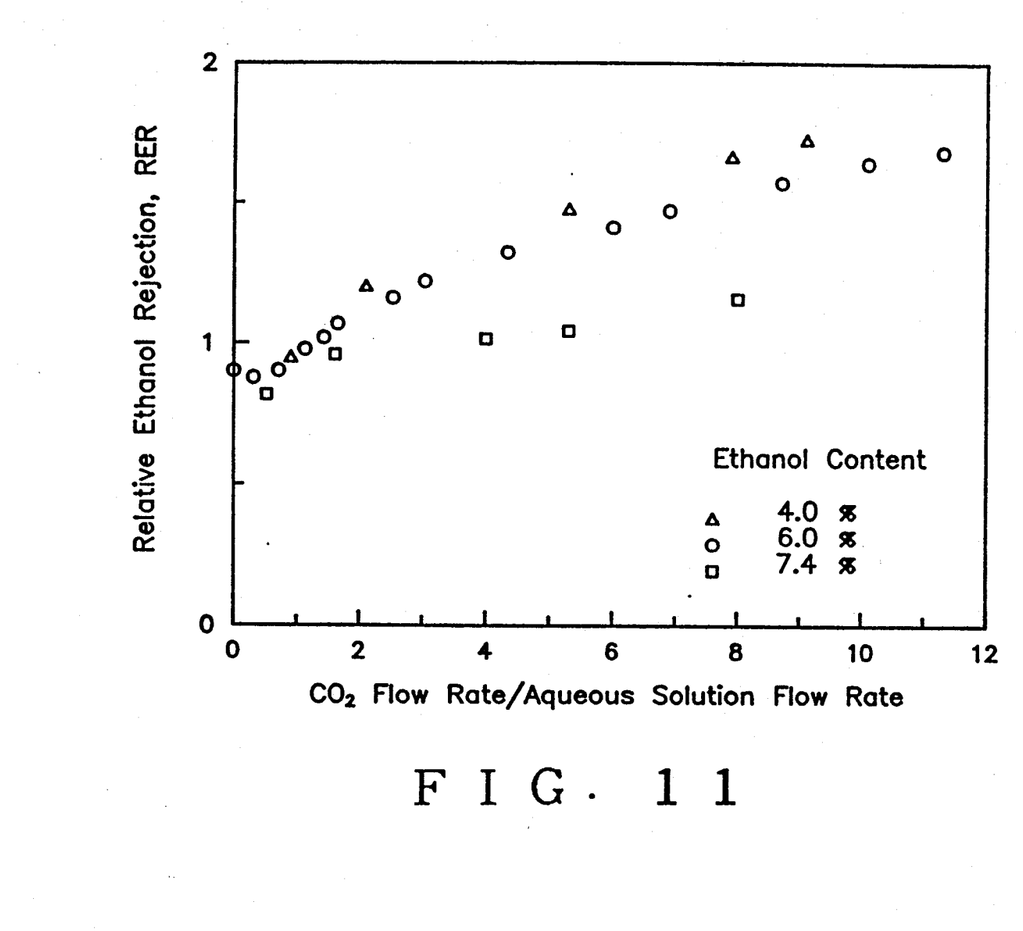
FIG. 11 is a plot which shows the effect of ethanol content on ethanol rejection at 304.5° K. and 74.8 atm.

FIG. 11 shows that the present process is more adequate to deal with lower ethanol content solutions as concerned with ethanol rejection. It was also observed that the permeation rate for the 4 wt % ethanol feed was about 20% more than that for the 6 wt % ethanol feed.

Effect of pH Value

Figure 12:
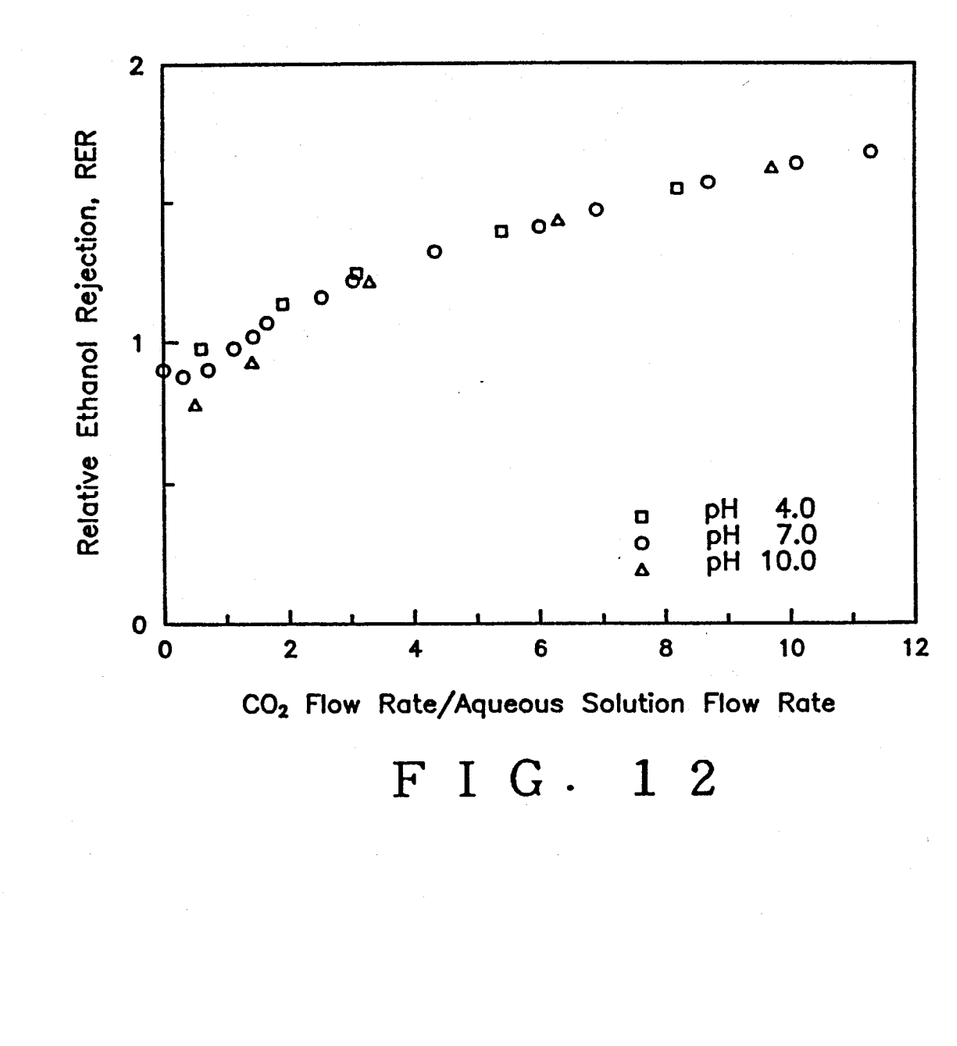
FIG. 12 is a plot which shows ethanol rejection for various ratios of $CO_2$ flow rate/aqueous solution flow rate.

The buffer solutions used in this example were prepared by adding 215 ml of dehydrated alcohol and the corresponding buffer into 2600 ml deionized water. Reidel-deHaen 33543 and Merck 948 were used as the buffers for preparation pH=4 and 10, respectively. FIG. 12 shows that the ethanol rejections for 60 wt % ethanol solution at 304.5° K. and 74.8 atm were not influenced significantly by pH value for the ratio of $CO_2$ flow rate to liquid flow rate larger than 2.0.

What is claimed is:

1. A process for separating ethanol from an aqueous solution by supercritical or near supercritical extraction in combination with reverse osmosis comprising contacting an ethanol containing aqueous solution with one side of a reverse osmosis membrane in the presence of a supercritical or near supercritical $CO_2$ having a pressure of 72.8–88.4 atm and a temperature of 26.5°–34° C., wherein the volumetric ratio of $CO_2$ to said ethanol containing aqueous solution at said pressure and temperature is higher than 1.8, and recovering a permeate solution having an ethanol concentration lower than that of said ethanol containing aqueous solution from the opposite side of said membrane.

2. A process in accordance with claim 1, wherein the pressure and temperature of said supercritical or near supercritical $CO_2$ are 74.8–81.6 atm and 31.1°–32.5° C., respectively, and the volumetric ratio of $CO_2$ to said ethanol containing aqueous solution is 4–12.

3. A process in accordance with claim 2, wherein the volumetric ratio of $CO_2$ to said ethanol containing aqueous solution is 8–10.

4. A process in accordance with claim 1, wherein the ethanol content of said ethanol containing aqueous solution is lower than 10 wt %.

5. A process in accordance with claim 4, wherein the ethanol content of said ethanol containing aqueous solution is 1–8 wt %.

6. A process in accordance with claim 1, wherein the pressure in the opposite side of said membrane is atmospheric pressure.

7. A process in accordance with claim 1, wherein the membrane is contacted with said ethanol containing aqueous solution under a pressure of 72.8–88.4 atm and a temperature of 26.5°–34° C. for a period of 3–4 fours before said $CO_2$ is introduced.

* * * * *